United States Patent
Martin et al.

(10) Patent No.: US 8,814,796 B2
(45) Date of Patent: Aug. 26, 2014

(54) SYSTEM AND METHOD FOR TISSUE ABLATION IN A BODY CAVITY

(75) Inventors: Gregory T. Martin, Somerville, MA (US); William L. Churchill, Bolton, MA (US); Daniel Beaudet, Lexington, MA (US); Robert F. Rioux, Ashland, MA (US)

(73) Assignee: Hologic, Inc., Marlborough, MA (US)

( * ) Notice: Subject to any disclaimer, the term of this patent is extended or adjusted under 35 U.S.C. 154(b) by 26 days.

(21) Appl. No.: 13/347,501

(22) Filed: Jan. 10, 2012

(65) Prior Publication Data
US 2013/0178738 A1 Jul. 11, 2013

(51) Int. Cl.
*A61B 8/00* (2006.01)

(52) U.S. Cl.
USPC .............................. 600/437; 606/41

(58) Field of Classification Search
USPC ........ 600/429–469; 606/22–50; 607/101–120
See application file for complete search history.

(56) References Cited

U.S. PATENT DOCUMENTS

| | | | |
|---|---|---|---|
| 5,351,692 A | 10/1994 | Dow et al. | |
| 5,527,331 A | 6/1996 | Kresch et al. | |
| 5,746,692 A | 5/1998 | Bacich et al. | |
| 5,769,880 A | 6/1998 | Truckai et al. | |
| 5,954,717 A | 9/1999 | Behl et al. | |
| 6,033,399 A | 3/2000 | Gines | |
| 6,080,149 A | 6/2000 | Huang et al. | |
| 6,156,033 A * | 12/2000 | Tu et al. | 606/41 |
| 6,648,839 B2 * | 11/2003 | Manna et al. | 601/2 |
| 6,736,814 B2 * | 5/2004 | Manna et al. | 606/50 |
| 6,813,520 B2 | 11/2004 | Truckai et al. | |
| 6,843,789 B2 | 1/2005 | Goble | |
| 7,223,267 B2 * | 5/2007 | Isola et al. | 606/52 |
| 7,517,346 B2 * | 4/2009 | Sloan et al. | 606/41 |
| 7,775,994 B2 | 8/2010 | Lockhart | |
| 7,799,022 B2 * | 9/2010 | Fernald et al. | 606/41 |
| 7,962,223 B2 * | 6/2011 | Young et al. | 607/101 |
| 8,007,449 B2 | 8/2011 | Kotmel et al. | |
| 8,152,801 B2 | 4/2012 | Goldberg et al. | |
| 2002/0040185 A1 * | 4/2002 | Atalar et al. | 600/423 |
| 2002/0111548 A1 * | 8/2002 | Swanson et al. | 600/407 |
| 2003/0078509 A1 | 4/2003 | Panescu | |
| 2003/0163131 A1 * | 8/2003 | Manna et al. | 606/50 |
| 2004/0073209 A1 * | 4/2004 | Manna et al. | 606/50 |
| 2005/0187512 A1 * | 8/2005 | Isola et al. | 604/22 |
| 2006/0135887 A1 | 6/2006 | Sampson et al. | |
| 2006/0178665 A1 * | 8/2006 | Sloan et al. | 606/41 |
| 2006/0293646 A1 * | 12/2006 | Whayne et al. | 606/27 |
| 2007/0142752 A1 | 6/2007 | Kotmel et al. | |
| 2007/0161905 A1 | 7/2007 | Munrow | |
| 2008/0015564 A1 | 1/2008 | Wham et al. | |
| 2008/0097467 A1 * | 4/2008 | Gruber et al. | 606/119 |
| 2008/0114354 A1 * | 5/2008 | Whayne et al. | 606/49 |
| 2008/0114355 A1 * | 5/2008 | Whayne et al. | 606/49 |
| 2009/0149753 A1 * | 6/2009 | Govari et al. | 600/439 |
| 2013/0072926 A1 | 3/2013 | Hong et al. | |

* cited by examiner

*Primary Examiner* — Sanjay Cattungal
(74) *Attorney, Agent, or Firm* — Robert P. Smith

(57) ABSTRACT

A tissue ablation system and method of forming same includes an ablation device having a substrate with an outer surface and energy transport elements coupled to the outer surface. The substrate is configured to have a shape that approximates an interior shape of a uterus. The system and method further including an energy source electrically coupled to the energy transport elements and at least one ultrasonic transducer positioned in a lateral region of the uterus.

17 Claims, 5 Drawing Sheets

SYSTEM AND METHOD FOR TISSUE ABLATION IN A BODY CAVITY

TECHNICAL FIELD

The present invention generally relates to systems and methods for tissue ablation in a body cavity and, more particularly, the invention relates to a tissue ablation system and method that measures the wall thickness of the body cavity prior to and/or during the ablation procedure.

BACKGROUND ART

Ablation of the interior lining of a body organ is a procedure which involves heating the organ lining to temperatures which destroy the cells of the lining, coagulate blood and/or denature tissue proteins. Existing methods for the energy transfer as part of effecting ablation include circulation of heated fluid inside the organ (either directly or inside a balloon), laser treatment of the organ lining, microwave heating of the tissue, high power ultrasound heating of the tissue or resistive heating using application of radiofrequency (RF) energy to the tissue to be ablated. These ablation procedures, however, are often carried out without direct endoscopic visualization. For example, ablation of the uterine lining or endometrium typically involves insertion of an elongate ablation device into the patient's cervix without the use of a hysteroscope. However, the thickness of the uterine wall may vary from patient-to-patient depending on a number of factors, such as the phase of the menstrual cycle and anatomical variability in the patient.

Consequently, the ablation depth and ablation profile are usually done by assumption since little data are available to help guide the physician as to how deep the tissue ablation needs to go. It is also difficult for a physician to find out when ablation has been carried out to a desired depth within the tissue during the procedure. Thus, in some instances, too much or too little tissue may be ablated during an ablation procedure.

SUMMARY OF EMBODIMENTS

In accordance with one embodiment of the invention, a tissue ablation system includes an ablation device having a substrate with an outer surface and energy transport elements coupled to the outer surface of the substrate. The substrate is configured to have a shape that approximates an interior shape of a uterus. The system further includes an energy source electrically coupled to the energy transport elements and at least one ultrasonic transducer positioned in a lateral region of the uterus.

In accordance with another embodiment of the invention, a method of forming a tissue ablation system includes providing an ablation device having a substrate with an outer surface and energy transport elements coupled to the outer surface of the substrate. The substrate is configured to have a shape that approximates an interior shape of a uterus. The method further includes electrically coupling an energy source to the energy transport elements and coupling the at least one ultrasonic transducer to the outer surface of the substrate in a lateral region of the substrate.

In accordance with another embodiment of the invention, a method of tissue ablation includes providing an ablation device having an a substrate with an outer surface and energy transport elements coupled to the outer surface of the substrate, and providing at least one ultrasonic transducer in a lateral region of the uterus. The substrate is configured to have a shape that approximates an interior shape of a uterus. The method further includes positioning the ablation device in contact with tissue to be ablated such that the at least one ultrasonic transducer is positioned in an area near a fallopian tube opening, and ablating the tissue with the ablation device.

In some embodiments, at least two ultrasonic transducers may be coupled to the outer surface of the substrate and positioned in opposing lateral regions of the substrate. At least two ultrasonic transducers may be coupled to the outer surface of the substrate, one positioned in the lateral region and one positioned in a medial region of the substrate. The system and method may further include a suction device fluidly coupled to the ablation device. The substrate may be an electrode carrier and the energy transport elements may be electrodes. The energy source may be a radiofrequency source, a microwave source, and/or an ultrasound source. Alternatively, or in addition, the energy source may be a fluid having a temperature of greater than about 45° C. At least a portion of the substrate may include a metallized fabric. The ultrasonic transducers may include a single element ultrasonic transducer. The system and method may further include one or more sensors positioned near the lateral region of the substrate and configured to sense a force applied to the outer surface of the substrate. The system and method may further include a spring coupled to the outer surface of the substrate and the ultrasonic transducer coupled to the spring. The system and method may further include a processor coupled to the ultrasonic transducer and coupled to the energy source. The processor may be configured to receive information from the ultrasonic transducer in order to determine a parameter and may be configured to terminate power to the energy source based on the parameter. The parameter may include ablation depth, time, temperature, tissue impedance, and/or total energy.

In accordance with another embodiment of the invention, a uterine cavity measurement device includes a uterine length measurement device having an elongate tube that includes a distal end, a proximal end, a hollow interior, and a slot extending longitudinally along its proximal end, and an elongate shaft that includes a distal end and a proximal end, and is configured to move within the hollow interior of the elongate tube. The uterine cavity measurement device also includes a control knob coupled to the elongate shaft and configured to move the elongate shaft within the elongate tube when the control knob moves along a length of the slot. The distal end of the elongate shaft is configured to protrude from the distal end of the elongate tube. The uterine cavity measurement device also includes at least one ultrasonic transducer positioned near the distal end of the elongate shaft and a spring coupled to the distal end of the elongate shaft and coupled to the at least one ultrasonic transducer.

In accordance with another embodiment of the invention, a uterine cavity measurement device includes a uterine length measurement device having an elongate tube that includes a distal end, a proximal end, a hollow interior, and a slot extending longitudinally along its proximal end, and an elongate shaft that includes a distal end and a proximal end, and is configured to move within the hollow interior of the elongate tube. The uterine cavity measurement device also includes a control knob configured to move the elongate shaft within the elongate tube when the control knob moves along a length of the slot. The distal end of the elongate shaft is configured to protrude from the distal end of the elongate tube. The uterine cavity measurement device also includes at least one ultrasonic transducer coupled to the distal end of the elongate shaft and a spring coupled to the proximal end of the elongate shaft and coupled to the control knob.

In some embodiments, the spring may be a constant force spring. The at least one ultrasonic transducer may include a single element piezoelectric ultrasonic transducer. The uterine cavity measurement device may further include a processor coupled to the at least one ultrasonic transducer. The processor may be configured to receive information from the at least one ultrasonic transducer in order to determine a thickness of tissue to be ablated and/or an ablation depth of tissue undergoing ablation.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

Prior to endometrial ablation, it would be beneficial to know the thickness of the uterine lining in order to prevent complications associated with removing too little or too much of the lining. Various embodiments of the present invention provide a system and method for tissue ablation that improves the ablation process by having one or more ultrasonic transducers strategically placed within a body cavity, such as the uterus, for measurement of a thickness of the body cavity lining prior to the ablation procedure. Ultrasonic transducers may be mounted on the ablation device, or a standalone diagnostic tool, or implemented separately. For example, ultrasonic transducers may be placed on a lateral region of an ablation device at its distal end which is being inserted into the uterine cavity to deliver energy. In this way, the ultrasonic transducers are positioned in a region near the fallopian tube openings where the uterine wall thickness is at a minimum. The ultrasonic transducers may be used to measure the amount of lining that needs to be removed before the ablation process begins in order to determine if the tissue thickness is sufficient to insulate organs outside the uterus from thermal injury or effects. In addition, the ultrasonic transducers may be used to monitor the thickness of the lining or to determine the ablation depth during the ablation process. Other embodiments of the present invention provide a method and device for use with an ablation system that includes one or more ultrasonic transducers strategically placed on a cavity measurement device, such as a uterine cavity measurement device or sound, that is used within the body cavity prior to the ablation procedure. Details of illustrative embodiments are discussed below.

Figure 1:
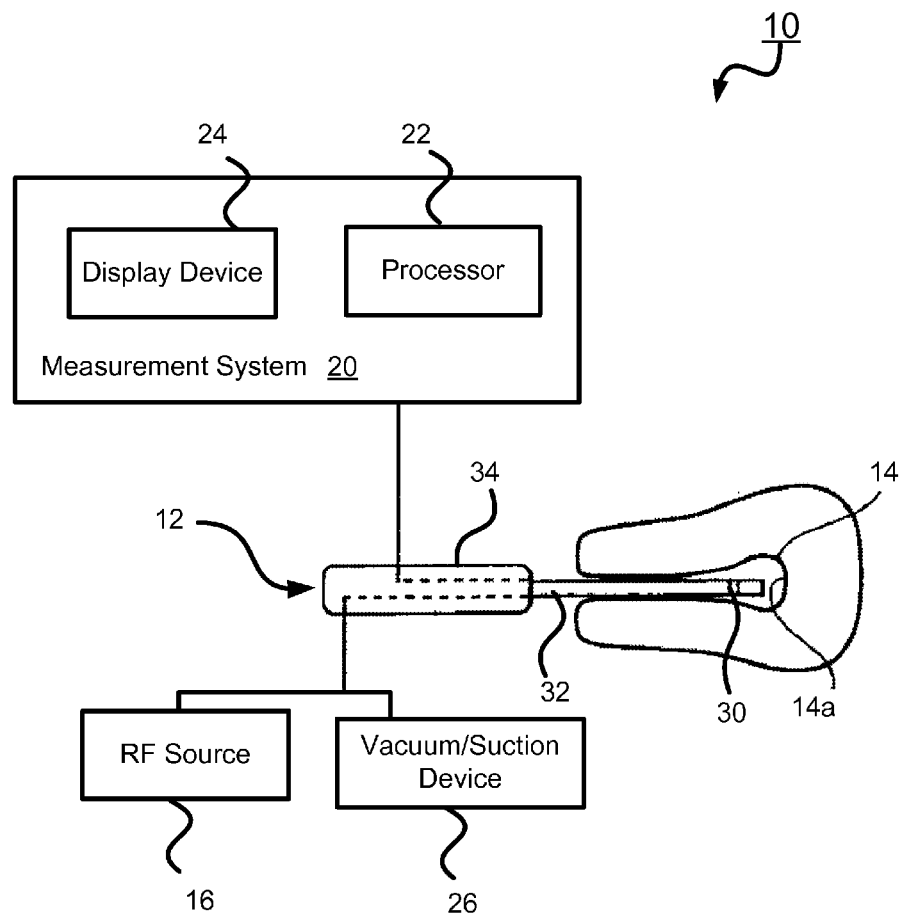
FIG. 1 schematically shows a tissue ablation system according to embodiments of the present invention.

FIG. 1 schematically shows a tissue ablation system 10 according to embodiments of the present invention. As shown, the tissue ablation system 10 includes an ablation device 12 configured to be inserted into a body cavity 14 and an energy source 16 electrically coupled to the ablation device 12 that is configured to deliver energy to an inner surface 14a of the body cavity 14 from the ablation device 12. Energy source 16 may include any form of energy known in the art for the purpose of ablation. For example, the energy source 16 may be a radiofrequency (RF) energy source electrically coupled to the ablation device 12 that is configured to deliver RF energy to the inner surface 14a by inducing current flow from the ablation device 12 to tissue to be ablated. The RF energy source may be a conventional general purpose electrosurgical power supply operating at a frequency in the range from 300 kHz to 9.5 MHz. Alternatively, or in addition, the energy source 16 may be a microwave energy source electrically coupled to the ablation device 12 that is configured to deliver microwave energy to the inner surface 14a or may be a microwave energy source electrically coupled to the ablation device 12 that is configured to deliver microwave energy to the inner surface 14a. In embodiments where the ablation device 12 includes an expandable material that contains fluid (gas and/or liquid) within the inner area of the material (e.g., a balloon), the energy source may be a fluid having a temperature of greater than about 45° C. so that the fluid heats the tissue to a sufficient temperature to be ablated. The ablation system 10 also includes one or more ultrasonic transducers 18 (shown in FIGS. 2 and 4, and discussed in more detail below) coupled to the ablation device 12 in such a way that the wall thickness (e.g., the uterine wall thickness) may be measured in an area which tends to have minimal thickness.

In general, ultrasonic transducers are capable of generating and receiving high frequency sound waves, typically between about 1 and 18 MHz, and can function by measuring the time interval between sending the signal and receiving the echo (e.g., using a processor coupled to the transducer) to determine the distance to one or more objects. Since there are density changes at the interface between the different layers or tissues in the body, ultrasonic transducers can determine the thickness of layers within the body. Thus, the ultrasonic transducers 18 can determine the thickness of various layers on the inner surface of the cavity 14, such as the thickness of the endometrial layer. In order for this measurement to be accurate, it is important that the ultrasonic transducer 18 make sufficient contact with the inner surface of the cavity 14.

Ultrasonic transducers 18 may be formed from a piezoelectric or similar material, single element material or a quartz crystal which converts electrical energy to ultrasonic energy and then, upon receiving the echo, turn the sound waves back into electrical energy which can be measured and displayed. Accordingly, the ultrasonic transducers 18 may be electrically coupled to a measurement system 20 that includes a processor 22 and an optional display device 24, such as a monitor or stereoscope, that may visually display information, e.g., thickness measurements. The processor may be configured to receive information from the ultrasonic transducers 18 in order to determine a parameter and may be configured to terminate or modulate power to the energy source 16 based on the parameter. For example, the parameter may be wall thickness, ablation depth, time, temperature, tissue impedance, and/or total energy. In addition, the ablation device 12 may be configured to withdraw fluids generated during ablation away from the inner surface 14a of the cavity 14 and into an interior of the ablation device 12. This may be done with the use of a suction device 26 that may or may not be fluidly coupled to the ablation device 12.

Figure 2:
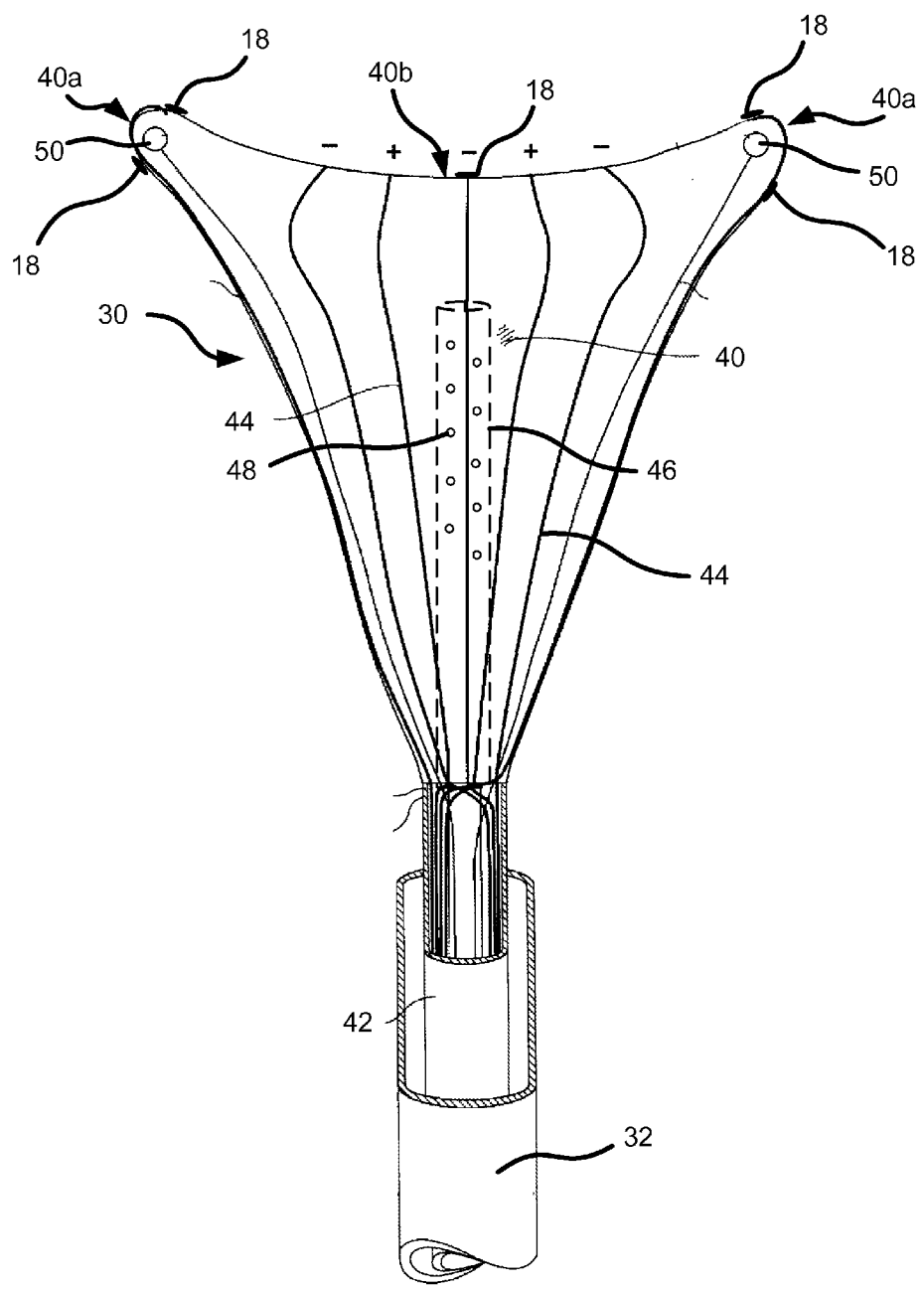
FIG. 2 schematically shows an ablation device according to embodiments of the present invention.
Figure 3:
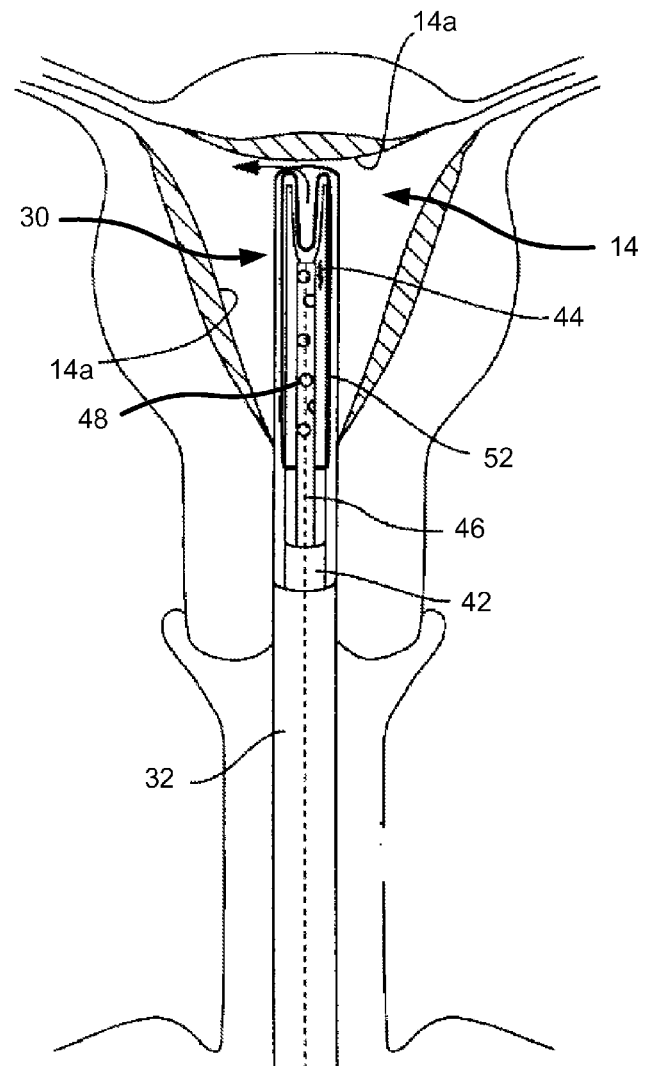
FIG. 3 schematically shows an ablation device in a closed position within the uterus according to embodiments of the present invention.
Figure 4:
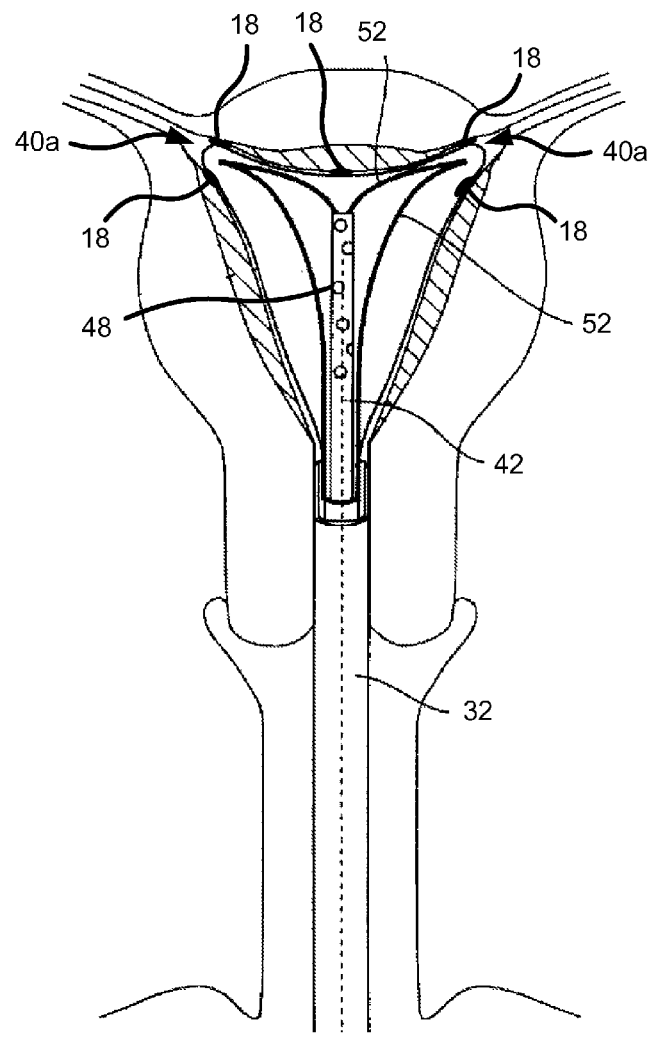
FIG. 4 schematically shows an ablation device in an opened position within the uterus according to embodiments of the present invention.

One exemplary ablation device 12 that may be used with the tissue ablation system 10 of the present invention is shown in FIGS. 2-4. Ablation devices of this type are shown and described in U.S. Pat. Nos. 5,769,880 and 6,554,780, each of which is incorporated by reference herein in its entirety. A similar device is commercially available under the name NovaSure® from Hologic, Inc., Bedford, Mass. As shown in FIG. 1, the ablation device 12 may include an applicator head 30, a shaft 32 having a hollow interior and configured to be inserted into the body cavity 14, and a handle 34. The applicator head 30 is slidably disposed within the shaft 32 to give the applicator head 30 a streamlined profile (such as shown in FIG. 3) to facilitate insertion of the ablation device 12 into the body cavity 14 (e.g., the uterine cavity). Once the applicator head 30 has been inserted into the body cavity 14, the handle 34 is manipulated to cause the applicator head 30 to extend from the distal end of the shaft 32 and to expand into an opened position (such as shown in FIGS. 2 and 4) so as to make contact with body tissue on the inner surface 14a of the body cavity 14.

As shown in more detail in FIG. 2, the applicator head 30 includes an electrode carrier 40 coupled to a distal end of a tube 42 that is slidably disposed within the shaft 32 and an array of electrodes 44 coupled to or formed within an outer surface of the substrate 40. Although an electrode carrier and an array of electrodes are further discussed below, principles of illustrative embodiments may apply to other substrate materials and other energy transport elements. For example, other energy transport elements may include optical fibers, antennas, wires, lumens to permit the passage of hot fluids, high powered ultrasound transducers, magnets, etc., and other substrate materials may include suitable materials that the energy transport elements may be coupled to or formed within its outer surface. Accordingly, discussion of electrode carriers and electrodes is exemplary and not intended to limit the scope of various embodiments of the invention.

The electrode carrier 40 is preferably formed of a stretchable metallized fabric material. Alternatively, the electrode carrier 40 may be formed from absorbent materials, such as sponge, foam, cotton, or cotton-like materials, or any other material having the desired characteristics. If the electrode carrier 40 is formed of a metallized fabric, an insulating layer may be formed, e.g., etched, into the fabric surface, leaving only the electrode regions exposed. The electrodes 44 may be electrically coupled to the energy source 16 to provide energy, e.g., bipolar RF energy, to the electrodes 44. The applicator head 30 may also include a suction tube 46 positioned within an interior of the electrode carrier 40 that has a plurality of holes 48 formed in its distal end. The suction tube 46 is fluidly connected to the suction device 26. During use, the electrode carrier 40 withdraws the fluids generated during ablation away from the inner surface 14a of the cavity 14 and into the suction tube 46.

Preferably, the electrode carrier 40 is configured to have a shape that approximates an interior shape of the uterus, with right and left lateral regions 40a that extend toward the fallopian tubes opening or os when the electrode carrier 40 is expanded in its open position during use. The one or more ultrasonic transducers 18 are coupled to the electrode carrier 40 in the lateral regions 40a and are configured to contact the inner surface 14a of the cavity 14 in an area which tends to have a minimal wall thickness to ensure that the ablation system 10 measures the lower limit of the wall thickness. Contact sensors 50 may be mounted to the electrode carrier 40, e.g., in the lateral regions 40a, in order to verify that the electrode carrier 40 is sufficiently contacting the inner surface 14a of the cavity 14 during use. One or more additional ultrasonic transducers 18 may also be coupled to the electrode carrier 40 in a medial region 40b, which allows the transducer 18 to be positioned within the cavity 14 in an area which tends to have its maximum wall thickness. Multiple measurements of the tissue thickness may be obtained one at a time or simultaneously. Processor 22 may be configured to use these measurements separately or collectively. Accordingly, the ultrasonic transducers 18 may measure the range of thicknesses of the various layers on the inner surface of the cavity 14 before the ablation procedure is begun to determine the amount of tissue removal that needs to be performed and can track the progress of the tissue removal during the ablation process.

Referring to FIGS. 3 and 4, during use, the distal end of the ablation device 12 is inserted into the cavity 14, e.g., uterus, with the shaft 32 covering the electrode carrier 40 and the electrode array 44 to keep the applicator head 30 in a streamlined condition. Once the applicator head 30 is within the cavity, the handle 34 (FIG. 1) is used to withdraw the shaft 32 which allows the electrode carrier 40 to deploy into its opened position, such as shown in FIG. 4. The electrode carrier 40 may be deployed with the help of an opening mechanism 52, e.g., spring or internal balloon, which is used to expand the electrode carrier 40 and cause it to be positioned into contact with the tissue on the inner surface 14a of the cavity 14. For example, as shown in FIG. 4, a spring mechanism 52 may be coupled to the distal end of the suction tube 46 and the distal end of the tube 42. Ultrasonic transducers 18 are activated in order to make one or more ultrasound measurements of the tissue thickness in selected areas prior to the initiation of energy in order to determine if the tissue thickness is sufficient to insulate organs outside the uterus from thermal injury or effects. The thickness of the uterine wall may be assessed prior to and/or during tissue ablation.

Suction device 26 (such as shown in FIG. 1) may be activated, which helps to draw uterine tissue into contact with the electrode carrier 40 and the electrodes 44. The energy source 16 supplies energy to the electrode array 44. For example, RF energy supplies RF energy to the electrode array 44, which causes the tissue to be heated as the RF energy passes from electrodes 44 to the tissue. During the ablation process, moisture can be released from the tissue. The suction device 26 helps to draw the moisture and other fluids from the uterine cavity into the suction tube 46. The measurement system 20 may provide parameters or feedback to the ablation system 10 so that the energy source 16 is turned off and the ablation process is stopped based on the parameter or feedback, e.g., once the desired tissue thickness has been removed, the desired tissue thickness remains, or the desired ablation depth has been achieved. Alternatively, the energy source 16 may be modulated during the ablation process based on the parameters from the measurement system 20, For example, the energy source 16 may be configured to ramp down energy from the energy source 16 as the desired tissue thickness is approached.

Figure 5:
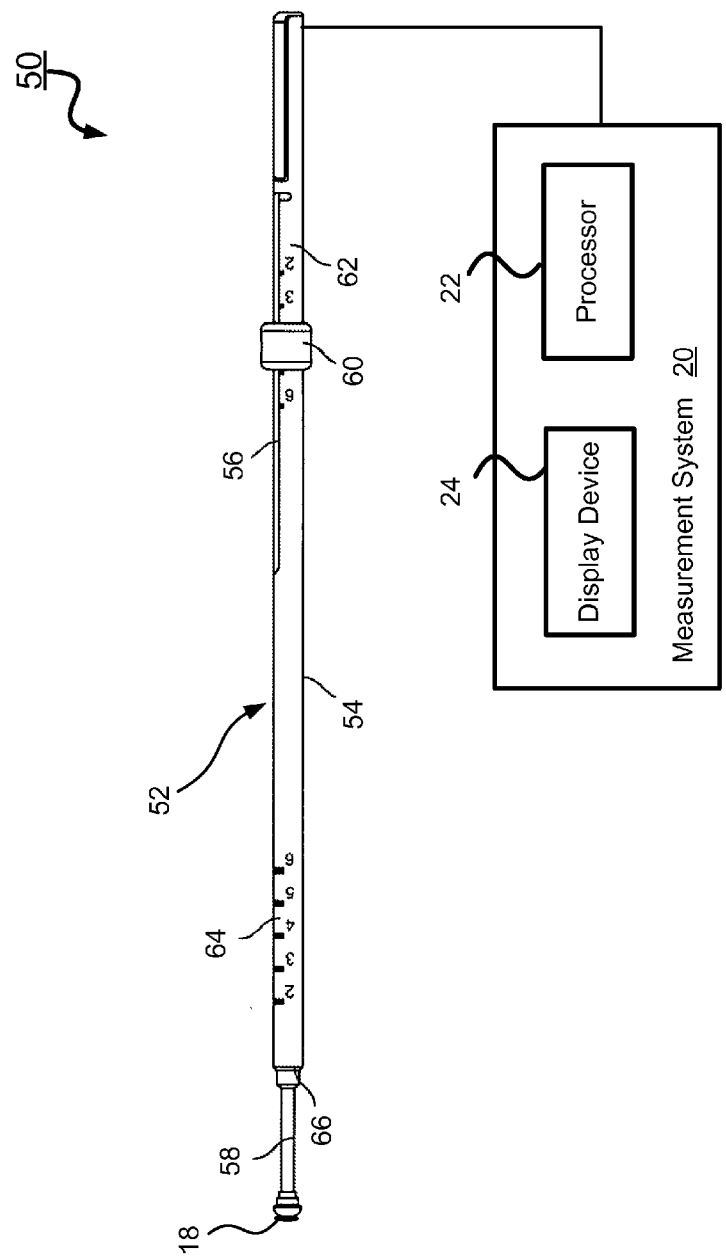
FIG. 5 schematically shows a uterine cavity measurement device according to embodiments of the present invention for use with a tissue ablation system.

FIG. 5 schematically shows a cavity measurement device 50 according to embodiments of the present invention for use with a tissue ablation system. As shown, the cavity measurement device 50 includes a cavity length measurement device 52 configured to be inserted into a body cavity 14 and one or more ultrasonic transducers 18 coupled to a distal end of the cavity length measurement device 52. As discussed above, the ultrasonic transducers 18 may be electrically coupled to a measurement system 20 that includes a processor 22 for determining a parameter based on information received from the ultrasonic transducers 18 and an optional display device 24, such as a monitor or stereoscope, that visually displays the parameter, e.g., thickness measurements. One exemplary uterine length measurement device is shown and described in U.S. Patent Publication No. 2007/0142752, which is incorporated by reference herein in its entirety. A similar device is commercially available under the name SureSound from Hologic, Inc., Bedford, Mass.

The cavity length measurement device 52 includes an elongate tube 54 having a slot 56 extending longitudinally in its proximal region, an elongate shaft 58 configured to move within a hollow interior of the elongate tube 54, and a control knob 60 coupled to the elongated shaft 58 and configured to move the elongate shaft 58 within the hollow interior of the elongate tube 54 when the control knob 60 moves along the length of the slot 56. As the control knob 60 moves along the length of the slot 56, the elongate shaft 58 moves between a retracted and an extended position. In the extended position, a distal end of the elongate shaft 58 is configured to protrude from a distal end of the elongate tube 54 and is configured to reach approximately the end of the cavity, such as the fundus of a uterine cavity.

The elongate tube 54 includes a first set of graduations 62 positioned near its proximal end. The first set of graduations 62 may provide a set of unit graduations configured to provide a length measurement of a body cavity, such as a uterine cavity. The elongate tube 54 may optionally include a second set of graduations 64 positioned near its distal end. The second set of graduations 64 may provide a set of unit graduations configured to provide a length measurement, e.g., of an endocervical canal. The slot 56 may extend substantially the length of the first set of graduations 62.

The elongate tube 54 includes a reduced diameter step portion 66 at its distal end. The step portion 66 has an outer diameter less than an outer diameter of the elongate tube 54. For example, the step portion 66 may be configured for insertion to approximately an internal cervical os of the endocervical canal, but configured such that the elongate tube 54 cannot easily advance beyond the internal cervical os while allowing the elongate shaft 58 to extend within the uterus. In this way, the step portion 66 may provide tactile feedback to a user for identifying the location of the internal cervical os of the endocervical canal and permit the measurement of the length of the uterus.

As mentioned above, the cavity measurement device 50 includes one or more ultrasonic transducers 18 coupled to the distal end of the cavity length measurement device 52. The cavity measurement device 50 is configured in such a way that the ultrasonic transducers 18 are able to make sufficient contact with the inner surface of the cavity 14 in order to make an accurate lining measurement, while preventing trauma to the lining, e.g., perforation of the uterine wall during a uterine length measurement procedure. This may be accomplished by using a spring (not shown), such as a constant force spring, in conjunction with the one or more ultrasonic transducers 18 so that an appropriate amount of force is used to place the transducers 18 in contact with the inner layer of the cavity 14. For example, a constant force spring may be coupled to the distal end of the cavity length measurement device 52 and then one or more ultrasonic transducer 18 coupled to the spring. Alternatively, the constant force spring may be coupled to the proximal end of the elongate shaft 58 and then the control knob 60 coupled to the spring. In this way, the ultrasonic transducers 18 may contact the inner layer of the cavity 14 with sufficient force to permit an accurate measurement of the lining without applying too much force that might cause the ultrasonic transducers to puncture the inner layer of the cavity 14.

Although FIG. 5 shows the cavity length measurement device 52 having one straight distal end component that one or more ultrasonic transducers 18 are coupled to, other configurations may also be used. For example, the cavity length measurement device 52 may have an angled distal end component or may have two or more prongs, each one having one or more ultrasonic transducers 18 coupled to its tip.

Although the above discussion involves using the tissue ablation system 10 or the cavity measurement device 50 within the uterus, principles of illustrative embodiments may apply to other body cavities. Accordingly, discussion of the uterus is exemplary and is not intended to limit the scope of various embodiments of the invention. In addition, although the above discussion discloses various exemplary embodiments of the invention, it should be apparent that those skilled in the art can make various modifications that will achieve some of the advantages of the invention without departing from the true scope of the invention.

What is claimed is:

1. A tissue ablation system comprising:
an ablation device including an elongate support member, the elongate support member having a proximal end and a distal end and defining a lumen therethrough in communication with an opening in the distal end, a substrate carried by the distal end, the substrate having an outer surface and configured to have a shape that approximates an interior shape of a uterus; and energy transport elements coupled to the outer surface of the substrate;
an energy source electrically coupled to the energy transport elements; and
at least one ultrasonic transducer coupled to the outer surface of the substrate so that when the substrate is positioned within the uterus, the at least one ultrasonic transducer is positioned in a lateral region of the uterus.

2. The tissue ablation system of claim 1, wherein at least two ultrasonic transducers are positioned on the outer surface of the substrate so that when the substrate is positioned within the uterus, the least two ultrasonic transducers are positioned in opposing lateral regions of the substrate.

3. The tissue ablation system of claim 1, further comprising at least one ultrasonic transducer positioned on the outer surface of the substrate so that when the substrate is positioned within the uterus, the at least one ultrasonic transducer is positioned in a medial region of the substrate.

4. The tissue ablation system of claim 1, wherein the substrate is an electrode carrier and the energy transport elements are electrodes.

5. The tissue ablation system of claim 1, wherein the energy source is a radiofrequency source.

6. The tissue ablation system of claim 1, further comprising a measurement system configured to generate a non-image based visual indication so that a user can track the progress of tissue removal during an ablation process.

7. The tissue ablation system of claim 6, wherein the measurement system is configured to modulate the energy source during the ablation process.

8. The tissue ablation system of claim 1, further comprising one or more sensors positioned near the lateral region of the substrate, the one or more sensors configured to sense a force applied to the outer surface of the substrate.

9. The tissue ablation system of claim 1, further comprising a spring coupled to the outer surface of the substrate, wherein the at least one ultrasonic transducer is coupled to the spring.

10. The tissue ablation system of claim 1, further comprising a processor coupled to the at least one ultrasonic transducer and coupled to the energy source, the processor configured to receive information from the at least one ultrasonic transducer in order to determine a parameter and configured to terminate power to the energy source based on the parameter, wherein the parameter includes ablation depth.

11. The tissue ablation system of claim 1, wherein the at least one ultrasonic transducer is fixedly coupled to the substrate.

12. The tissue ablation system of claim 1, further comprising a processor coupled to the at least one ultrasonic transducer, the processor configured to calculate a tissue thickness based on density information from the at least one ultrasonic transducer.

13. The tissue ablation system of claim 12, wherein the processor configured to calculate tissue thickness for a plurality of tissue layers.

14. The tissue ablation system of claim 1, wherein the shape includes right and left lateral regions that extend toward each fallopian tube.

15. A method of ablating tissue in a uterus, comprising:
- accessing the uterus transcervically with an elongate tubular device;
- distending the uterus with the elongate tubular device by expanding a working end of the elongate tubular device, wherein the working end includes a substrate and an ultrasonic transducer coupled to an outer surface of the substrate, and wherein expanding a working end of the elongate tubular device includes positioning the ultrasonic transducer in a lateral region of the uterus;
- receiving an indication the ultrasonic transducer is in contact with the tissue to be ablated;
- applying a vacuum to remove fluid through the tubular device;
- receiving a non-image based visual indication of a thickness of the tissue to be ablated;
- activating the elongate tubular device to ablating tissue in the uterus;
- maintaining contact between the ultrasonic transducer and the tissue to be ablated during at least a portion of the ablating step; and
- deactivating the elongate tubular device upon achieving a desired ablation depth.

16. The method of claim 15, further comprising generating a non-image based indication of a thickness of the tissue to be ablated using the at least one ultrasonic transducer.

17. The method of claim 15, further comprising modulating the ablation based on ablation depth.

\* \* \* \* \*